US012630437B2

(12) United States Patent (10) Patent No.: US 12,630,437 B2
Laksmana et al. (45) Date of Patent: May 19, 2026

(54) PROCESS FOR MANUFACTURING HIGH-PURITY MAGNESIUM OXIDE

(71) Applicant: PURAC BIOCHEM B.V., Gorinchem (NL)

(72) Inventors: Fesia Lestari Laksmana, Gorinchem (NL); Raymon Frediansyah, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 784 days.

(21) Appl. No.: 17/919,336

(22) PCT Filed: Apr. 20, 2021

(86) PCT No.: PCT/EP2021/060178
§ 371 (c)(1),
(2) Date: Oct. 17, 2022

(87) PCT Pub. No.: WO2021/214025
PCT Pub. Date: Oct. 28, 2021

(65) Prior Publication Data
US 2023/0202856 A1     Jun. 29, 2023

(30) Foreign Application Priority Data

Apr. 20, 2020     (EP) ..................................... 20170431

(51) Int. Cl.
*C01F 5/10*          (2006.01)
*B01J 21/10*         (2006.01)
(Continued)

(52) U.S. Cl.
CPC ................ *C01F 5/10* (2013.01); *C07C 51/02* (2013.01); *C07C 59/08* (2013.01); *C12P 7/56* (2013.01);
(Continued)

(58) Field of Classification Search
CPC . C01F 5/10; C07C 51/02; C07C 59/08; C12P 7/56; C01P 2004/61; C01P 2004/62; Y02P 20/10
(Continued)

(56) References Cited

U.S. PATENT DOCUMENTS 3,338,668 A * 8/1967 Lyons ....................... C01F 5/34
423/498
5,106,608 A     4/1992 Retschnig et al.
(Continued)

FOREIGN PATENT DOCUMENTS

CN          100417596 C     9/2008
CN          106163989 A     11/2016
(Continued)

OTHER PUBLICATIONS

Jun. 16, 2021 International Search Report issued in International Patent Application No. PCT/EP2021/060178.
(Continued)

*Primary Examiner* — Cam N. Nguyen
(74) *Attorney, Agent, or Firm* — Sunit Talapatra; Foley & Lardner LLP

(57) ABSTRACT

A process for converting magnesium chloride into magnesium oxide having the steps of: subjecting a magnesium chloride solution to a spray drying step in a spray-drying apparatus at a temperature of 300-475° C., resulting in the formation of a spray-dried product having 10-80 wt. % magnesium oxide and 20-90 wt. % of the total of magnesium hydroxychloride and magnesium chloride, subjecting the product of the spray drying step to a roasting step in a roaster at a temperature of 600-900° C. in the presence of water, resulting in the formation of a product having at least 98 wt. % of MgO, and less than 2 wt. % of the total of magnesium hydroxychloride and magnesium chloride, wherein the per-
(Continued)

centages of MgO, magnesium hydroxychloride and magnesium chloride, are calculated on the total of MgO, magnesium hydroxychloride and magnesium chloride.

20 Claims, 1 Drawing Sheet

(51) Int. Cl.

| | |
|---|---|
| *C07C 51/02* | (2006.01) |
| *C07C 59/08* | (2006.01) |
| *C12P 7/40* | (2006.01) |
| *C12P 7/56* | (2006.01) |

(52) U.S. Cl.
CPC ...... *C01P 2004/61* (2013.01); *C01P 2004/62* (2013.01)

(58) Field of Classification Search
USPC ........................................................ 423/639
See application file for complete search history.

(56) References Cited

U.S. PATENT DOCUMENTS

| | | | | |
|---|---|---|---|---|
| 6,214,310 | B1 | 4/2001 | Lebl | |
| 10,106,821 | B2 * | 10/2018 | De Vries | C01F 5/10 |
| 11,261,467 | B2 * | 3/2022 | De Haan | C01F 5/10 |
| 11,326,188 | B2 * | 5/2022 | De Haan | C01B 7/035 |
| 11,326,189 | B2 * | 5/2022 | De Haan | C01B 7/035 |
| 2002/0159946 | A1 | 10/2002 | Lebl | |
| 2023/0136575 | A1 | 5/2023 | Abuelhaiga et al. | |

FOREIGN PATENT DOCUMENTS

| | | | |
|---|---|---|---|
| CN | 110015671 | A | 7/2019 |
| CN | 110182832 | A | 8/2019 |
| JP | S55-014048 | B1 | 4/1980 |
| JP | H03-501380 | A | 3/1991 |
| JP | 2003-033159 | A | 2/2003 |
| JP | 2023-519749 | A | 5/2023 |
| KR | 10-2016-0140864 | A | 12/2016 |
| WO | 00/17378 | A2 | 3/2000 |
| WO | 2013/025106 | A1 | 2/2013 |
| WO | 2013/093028 | A1 | 6/2013 |
| WO | 2015/150325 | A1 | 10/2015 |
| WO | WO-2021/199049 | A1 | 10/2021 |

OTHER PUBLICATIONS

Jun. 16, 2021 Written Opinion issued in International Patent Application No. PCT/EP2021/060178.

Mar. 20, 2024 Office Action issued in Korean Patent Application No. 10-2022-7040133.

English Translation of Jan. 2, 2024 Office Action issued in Chinese Patent Application No. 2021800296719.

* cited by examiner

PROCESS FOR MANUFACTURING
HIGH-PURITY MAGNESIUM OXIDE

The present invention pertains to a process for manufacturing high-purity magnesium oxide from magnesium chloride solutions. The invention also pertains to an integrated process comprising a fermentation step, a separation step, and a step for converting a magnesium chloride solution into high-purity magnesium oxide.

Methods for manufacturing carboxylic acids through fermentation are known in the art. In these methods, a base is often added to keep the pH of the fermentation medium at the desired value. This results in the carboxylic acid being obtained in the form of a salt, e.g. a magnesium salt. Upon recovering the carboxylic acid, salt solutions, e.g., magnesium salt solutions are obtained, which require further processing. Preferably, the salt solutions are processed to form materials which are suitable for recycling to earlier steps of the fermentation. In particular it is preferred to process the salt solution to form a base that can be used for pH control in the fermentation.

For example, WO00/17378 describes a method for manufacturing lactic acid, wherein in a fermentation process a magnesium lactate solution is prepared. The magnesium lactate solution is acidified with HCl to yield a solution comprising lactic acid in a magnesium chloride solution. The lactic acid is recovered from the solution. The resulting magnesium chloride solution may be processed by subjecting it to a thermohydrolysis step at a temperature of at least 500° C. to react the magnesium chloride with water to yield magnesium oxide powder and hydrochloric acid. The heat required for the thermohydrolytic reaction is provided by the in situ combustion of fuel.

WO2013/025106 describes a method for manufacturing carboxylic acids through a process comprising the steps of acidifying a magnesium salt of a carboxylic acid with HCl to form an acid and a magnesium chloride solution, and isolating the acid from the solution through precipitation. It is indicated that the magnesium chloride solution may be processed through thermal decomposition.

WO2013/093028 describes a method for manufacturing carboxylic acids through a process comprising the steps of acidifying a magnesium salt of a carboxylic acid with HCl to form an acid and a magnesium chloride solution, and isolating the acid from the solution through extraction followed by back extraction. It is indicated that the magnesium chloride solution may be processed through thermal decomposition.

In the references cited above, the magnesium chloride solutions are processed by providing the solution to a thermal decomposition step, where the magnesium chloride reacts with water from the solution to form solid magnesium oxide and a gas stream comprising water and HCl.

A problem with the thermal decomposition processes described in these references is that the magnesium oxide recovered from the spray drying step may be of insufficient purity to recycle it to the fermentation process, either directly or after conversion into magnesium hydroxide. More specifically, it has been found that the chloride content of the magnesium oxide content may be so high that the chloride detrimentally affects the fermentation process. For example, it has been found that when a magnesium chloride solution is subjected to a spray drying step in a spray-drying apparatus at a temperature of 500-600° a product is formed with a magnesium oxide content of 97 wt. %, the balance being magnesium chloride and magnesium hydroxychloride. In this context one should be aware that during fermentation magnesium oxide (or its derivative magnesium hydroxide) is added to the process in an amount which is of the order of one mole magnesium per mole carboxylic acid formed. This means that even minor amounts of contaminants in the magnesium oxide will end up in the fermentation medium in substantial amounts.

There is thus need in the art for a process for manufacturing high-purity magnesium oxide from a magnesium chloride solution. The present invention provides such a process.

The invention pertains to a process for converting magnesium chloride into magnesium oxide comprising the steps of subjecting a magnesium chloride solution to a spray drying step in a spray-drying apparatus, at a temperature in the range of 300-475° C., resulting in the formation of a spray-dried product comprising 10-80 wt. % magnesium oxide and 20-90 wt. % of the total of magnesium hydroxychloride and magnesium chloride, subjecting the product of the spray drying step to a roasting step in a roaster at a temperature of 600-900° C. in the presence of water, resulting in the formation of a product comprising at least 98 wt. % of MgO, and less than 2 wt. % of the total of magnesium hydroxychloride and magnesium chloride, wherein the percentages of MgO, magnesium hydroxychloride and magnesium chloride are calculated on the total of these three compounds.

It has been found that the combination of a relatively mild spray drying step with a high-temperature roasting step makes it possible to obtain magnesium oxide with a high purity in an efficient manner. Further advantages from the present invention and specific embodiments thereof will become apparent from the further specification.

More specifically, it has been found that the process according to the invention, with a spray-drying temperature of 300-475° C. followed by roasting at a temperature of 600-900° C., results in the formation of a product comprising at least 98 wt. % of MgO, and less than 2 wt. % of the total of magnesium hydroxychloride and magnesium chloride, wherein the percentages of MgO, magnesium hydroxychloride and magnesium chloride are calculated on the total of these three compounds. When the product of a spray-drying step carried out at a temperature of 500-600° C., which thus has a much lower chloride content, is subjected to a roasting step under the same conditions, a magnesium oxide product is obtained with the same chloride content. Apparently, and surprisingly, the product obtained from spray-drying at 300-475° C. can be converted into high-purity MgO under the same conditions as a product obtained from spray-drying at 500-600° C., despite its higher chloride content. In the process of the present invention, the product of the spray-drying step is provided directly to the roasting step, without any intermediate steps such as washing or rehydration steps.

It is noted that the production of high-purity magnesium oxide has been described also outside the context of fermentation processes. For example, CN110015671 describes a process for manufacturing high-purity magnesium oxide in which bischofite (MgCl2·6H2O) is dehydrated by spraydrying of a bischofite solution at 650-750° C. to form anhydrous magnesium chloride, after which the anhydrous magnesium chloride is reacted with water in a rotary kiln to produce magnesium oxide. Thus, in this reference, the spray-drying step is carried out at a much higher temperature than in the process according to the invention, and is used to manufacture anhydrous magnesium chloride, and not to partially convert the magnesium chloride to a product containing specific amounts of magnesium oxide and magnesium(hydro)chloride. CN100417596 describes a method for manufacturing high-purity magnesium oxide in which magnesium chloride hydrate is subjected to a pyrolysis step in a sealed pyrolysis stove at a temperature of 400-600° C. for 0.5-3 hours. The product is subjected to a washing step with water to remove aqueous impurities. In this step, the MgO is converted to Mg(OH)2. After a solid-liquid separation step, the product is subjected to a roasting step for 1.5-3.5 hours at a temperature of 500-700° C.

The process will be discussed in more detail below.

In the following, reference will be made to the following figures, without being limited thereto or thereby.

Figure 1:
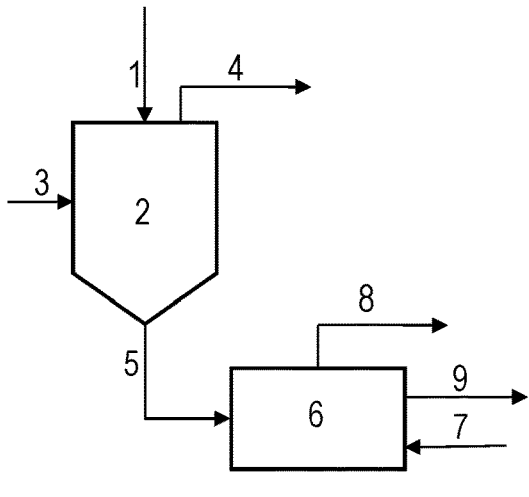
FIG. 1 illustrates the process according to the invention.

The first step in the process according to the invention is the step of subjecting a magnesium chloride solution to a spray drying step in a spray-drying apparatus at a temperature in the range of 300-475° C., resulting in the formation of a spray-dried product comprising 10-80 wt. % magnesium oxide and 20-90 wt. % of the total of magnesium hydroxychloride and magnesium chloride, calculated on total solid product.

It is preferred that the first step encompasses subjecting a magnesium chloride solution to a spray drying step in a spray-drying apparatus, at a temperature in the range of 300-475° C., resulting in the formation of a spray-dried product comprising 30-80 wt. % magnesium oxide and 20-70 wt. % of the total of magnesium hydroxychloride and magnesium chloride The magnesium chloride solution subjected to the spray drying step in the process according to the invention generally has a magnesium chloride concentration of 5-48 wt. %, in particular 15-48 wt. %. If the magnesium chloride solution has a concentration which is low, e.g., less than 5 wt. % or less than 15 wt. %, the amount of water to be evaporated in the spray drying step is so high that the process is not attractive from an energy point of view. On the other hand, at magnesium chloride concentrations above 48 wt. % there is a risk of precipitation of magnesium chloride in the spray drying nozzle. In general, it is preferred for the magnesium chloride solution to have a concentration which is as high as possible, without precipitation of magnesium chloride in the nozzle occurring. Therefore, it is preferred for the magnesium chloride solution to have a magnesium chloride concentration in the range of 18-48 wt. %, in particular 23-48 wt. %, more in particular 30-48 wt. %, even more in particular in the range of 35-47 wt. %.

It is preferred for the magnesium chloride solution used in the process according to the invention to contain only limited amounts of other compounds than magnesium chloride and water, as the aim is to prepare magnesium oxide with high purity. More in particular, it is preferred for the magnesium chloride solution to contain at least 95 wt. % of magnesium chloride and water, in particular at least 98 wt. %, more in particular at least 99 wt. %.

The temperature of the magnesium chloride solution as provided to the spray-drying step is not critical, and may vary between room temperature and 140° C. Higher temperatures and more concentrated magnesium chloride solutions are preferred, because the result in less energy consumption in the spray drying step. Higher temperatures can be obtained, e.g., by heating the solution in a heat exchange step using hot gas or hot liquid, in manners known in the art. It may be preferred for the magnesium chloride solution as provided to the spray-drying step to have a temperature in the range of 50-140° C., in particular in the range of 70-135° C., more in particular in the range of 90-130° C.

The magnesium chloride solution is provided to a spray drying step in a spray-drying apparatus at a temperature in the range of 300-475° C., preferably 350-450° C. Spray-drying processes and apparatus are known in the art. In a spray drying apparatus, the feed to be spray dried is provided to a spray tower, and sprayed through a nozzle to form small droplets. The droplets fall down through hot gas, and solidify in the process, under the evaporation of water. Further, magnesium chloride is partially converted to magnesium oxide.

In the process according to the invention, the spray-dying step is carried out at a temperature in the range of 300-475° C., preferably 350-450° C. The temperature is determined at the location of the spray-drying nozzle. If the temperature is too low, the conversion of magnesium chloride into magnesium oxide will be insufficient. If the temperature is too high, too much magnesium chloride may be formed, which will detrimentally affect the purity of the final product. It is preferred for the temperature in to be in the range of 350-450° C., in particular 375 to 450° C., more in particular 375-420° C. The temperatures given here are gas temperatures.

The residence time in the spray-drying apparatus, defined as the time between the moment that the droplet leaves the nozzle and the moment that the solid particles reach the bottom of the unit, generally is in the range of 1 to 60 seconds, in particular in the range of 3 to 30 seconds. The residence time is governed by the height of the spray tower and the flow velocity and direction of any gas streams provided to the spray tower.

The specified degree of conversion obtained in the spray-drying step can be obtained by selecting a combination of temperature and residence time suitable to obtain said conversion. Higher temperatures and longer residence times will result in higher degrees of conversion. It is within the scope of the skilled person to determine a suitable combination of residence time and temperature to achieve the desired degree of conversion based on his common general knowledge and the teachings of the present specification.

Depending on the configuration of the spray-drying apparatus, it may be that the particles have additional residence time at the bottom of the spray-dryer, e.g. by having countercurrent gas flow, a fluidized bed, or a rotating bed, before they are moved on to the roaster. It has been found that the additional residence time at the bottom of the spray-dryer does not materially affect conversion, presumably because the particles are not in intensive contact with the hot gas. It is generally preferred, however, for the particles to have a residence time at the bottom of the spray-dryer of at most 60 minutes, in particular at most 30 minutes, more in particular at most 15 minutes, or at most 10 minutes, or at most 5 minutes, for reasons of processing efficiency.

In the spray-drying step, gas is provided to the unit to provide the necessary temperature and airflow. The nature of the gas is not critical. Generally hot combustion gases are provided, e.g., by the burning of natural gas, biogas, hydrogen, or syngas. Gas is also withdrawn from the unit. The gas that is withdrawn from the unit contains HCl generated by the decomposition of the magnesium chloride into magnesium oxide. The gas that is withdrawn from the unit also contains water evaporated from the particles.

The spray-drying step generates solid particles which comprise 10-80 wt. %, in particular 30-80 wt. % magnesium oxide and 20-90 wt. %, in particular 20-70 wt. % of the total of magnesium hydroxychloride and magnesium chloride, calculated on total solids content. If the conversion into magnesium oxide is too low, it will not be possible to attain the conversion of at least 98 wt. % of magnesium oxide in the second step. If the conversion into magnesium oxide is above 80 wt. %, process efficiency will be affected. It is preferred for the product from the spray-drying step to comprise 40-80 wt. % magnesium oxide and 20-60 wt. % of the total of magnesium hydroxychloride and magnesium chloride, in particular 45-75 wt. % magnesium oxide and 25-55 wt. % of the total of magnesium hydroxychloride and magnesium chloride, more in particular 50-70 wt. % magnesium oxide and 30-50 wt. % of the total of magnesium hydroxychloride and magnesium chloride, still more in particular 55-70 wt. % magnesium oxide and 45-30 wt. % of the total of magnesium hydroxychloride and magnesium chloride, all calculated on total solids content. The degree of conversion can be determined by selecting a suitable spray-drying temperature and residence time.

The product from the spray-drying step is subjected to a roasting step in a roaster at a temperature of 600-900° C. in the presence of water, resulting in the formation of a product comprising at least 98 wt. % of MgO, and less than 2 wt. % of the total of magnesium hydroxychloride and magnesium chloride, calculated on the total of these three compounds. A temperature of less than 600° C. will not suffice to obtain the necessary degree of conversion within a reasonable time frame. It is preferred for the temperature to be at least 700° C., in particular at least 750° C., as higher temperatures will reduce the time necessary to obtain the desired conversion. A temperature of more than 900° C. will require such high energy input that it is generally not attractive from a commercial point of view. Further, the product will be less reactive. It may be preferred for the temperature in the roaster to be at most 850° C.

The residence time in the unit is selected such that the desired degree of conversion is obtained at the desired temperature. As will be evident to the skilled person, lower temperatures will require longer residence times to get the desired degree of conversion. In general, the residence time in the roaster will be between 10 minutes and 4 hours, more specifically between 15 minutes and 2 hours, in some embodiments between 30 minutes and 90 minutes. It is within the scope of the skilled person to determine a suitable combination of residence time and temperature to achieve the desired degree of conversion based on his common general knowledge and the teachings of the present specification.

The roasting step is carried out in the presence of water, to allow reaction of the magnesium chloride and magnesium hydroxychloride into magnesium oxide. The amount of water is not critical, as long as sufficient water is present to allow the reaction to take place. Excess water will easily be removed with the roast gas. As a general range, a value of 0.1-50 mol % water, in particular 0.1-15 mol % water, more in particular 0.1-10 mol % water, calculated on the composition of the roast gas provided to the roasting step, may be mentioned.

In the roasting step, gas is provided to the unit to provide the necessary temperature. The nature of the gas is not critical. In one embodiment hot combustion gases are provided, e.g., resulting from the burning of natural gas, biogas, hydrogen, and syngas. An advantage of this source is that the gas stream inherently contains water. Gas is also withdrawn from the unit. The gas that is withdrawn from the unit contains HCl generated by the decomposition of the magnesium (hydroxyl)chloride into magnesium oxide, e.g., in an amount of 0.3-5 mole %, calculated on the composition of the gas leaving the unit.

The product obtained from the process according to the invention comprises at least 98 wt. % of MgO, and less than 2 wt. % of the total of magnesium hydroxychloride and magnesium chloride, calculated on the total of these three components. It is possible for the process according to the invention to manufacture magnesium oxide of even higher purity, comprising, e.g., at least 98.5 wt. % of MgO, and less than 1.5 wt. % of the total of magnesium hydroxychloride and magnesium chloride, or even at least 99 wt. % of MgO, and less than 1 wt. % of the total of magnesium hydroxychloride and magnesium chloride, calculated on the total of these three components.

Depending on the composition of the starting material, the solid product may contain further contaminants. It is, however, preferred for the total of MgO, magnesium hydroxychloride and magnesium chloride to make up at least 95 wt. % of the solid product, in particular at least 98 wt. %, more in particular at least 99 wt. %. It is particularly preferred for the solid product to comprise at least 98 wt. % of MgO, and less than 2 wt. % of the total of magnesium hydroxychloride and magnesium chloride, calculated on solid product. It is particularly preferred for the process according to the invention to manufacture magnesium oxide of even higher purity, comprising, e.g., at least 98.5 wt. % of MgO, and less than 1.5 wt. % of the total of magnesium hydroxychloride and magnesium chloride, or even at least 99 wt. % of MgO, and less than 1 wt. % of the total of magnesium hydroxychloride and magnesium chloride, calculated on total solid product.

The process according to the invention has been found to result in magnesium oxide product particles having a relatively narrow particle size distribution. The particle size distribution can be characterized by the D-values D10, D50, and D90. D10 is the diameter at which 10% of the mass of a sample is comprised of particles with a diameter below this value. The D50 is the diameter at which 50% of the sample mass has a diameter below this value and 50% of the sample mass has a diameter above this value. D90 is the diameter at which 90% of the sample mass has a diameter below this value. The D-values can be determined by methods known in the art, e.g., laser diffraction on a dispersion of the product in a saturated MgO solution.

In one embodiment, the particles obtained by the process according to the invention have a D50 in the range of 0.5 to 20 micron, in particular in the range of 2 to 10 micron.

The magnesium oxide obtained by the method according to the invention has a high reactivity, as can be quantified by the citric acid reactivity. More in particular, the magnesium oxide has a citric acid reactivity in the range of 75-400 s, preferably 100-350 s, and specifically between 150 and 300 s. Citric acid reactivity is determined as follows: An (0.4 eq/L/25.61 g/L) citric acid solution is prepared containing phenolphthalein (30 mg) as indicator. The acid solution was shaken for at least one hour at 30° C. 1±0.01 g of the powdered MgO sample was transferred into 50 ml of the acid solution at 30° C. and shaken until the colour of the slurry changed from white to pink. The time taken for the slurry to change the colour is the citric acid reactivity. The method is analogous to that described in E. M. van der Merwe, Hydration of medium reactive industrial magnesium oxide with magnesium acetate, thermogravimetric study, Journal of Thermal Analysis and calorimetry, Vol 77 (2004) 49-56.

The invention also pertains to a new magnesium oxide product, which is characterized by the following parameters:

it comprises at least 98 wt. % of MgO, and less than 2 wt. % of the total of magnesium hydroxychloride and magnesium chloride, calculated on total solid product, in particular at least 98.5 wt. % of MgO, and less than 1.5 wt. % of the total of magnesium hydroxychloride and magnesium chloride, calculated on total solid product, more in particular at least 99 wt. % of MgO, and less than 1 wt. % of the total of magnesium hydroxychloride and magnesium chloride, calculated on total solid product.

it has a D50 in the range of 0.5 to 20 micron, in particular in the range of 2 to 10 micron, it has a citric acid reactivity in the range of 75-400 s, preferably 100-350 s, and specifically between 150 and 300 s.

The product preferably comprises less than 0.5 wt. % of other components than MgO, magnesium hydroxychloride and magnesium chloride, in particular less than 0.1 wt. % of other components. The new magnesium oxide product is attractive for various uses in view of its high purity an reactivity.

Spray-drying and roasting apparatus is known in the art, and requires no further elucidation here. Apparatus comprising both a spray-drying zone and a roasting zone are also known in the art. Reference is made, e.g., to U.S. Pat. No. 6,214,310 and US2002/0159946.

U.S. Pat. No. 6,214,310 focuses on the regeneration of pickling acids which are used in steel manufacture. It describes a process wherein partial conversion of the metal salt takes place in the spray drying zone with final conversion in the roasting zone. The spray-drying zone is operated at a temperature of 500-600° C. The conversion of magnesium chloride is not described and the degree of conversion in the spray drying zone is not specified.

US2002/0159946 describes a spray-roasting process wherein a metal salt solution is sprayed, and water is evaporated in a first stage to form metal salt particles. The metal salt particles are subsequently heated in a conversion stage at a low temperature to convert the salt into oxides.

The process according to the invention yields a magnesium oxide with high purity and low chloride content, which is suitable for use as neutralization agent in a fermentation process for the manufacture of carboxylic acids. The invention thus also pertains to a process for manufacturing carboxylic acids through fermentation employing a magnesium oxide obtained through the process according to the invention. The invention also pertains to an integrated process comprising a fermentation step, a separation step, and a step for converting a magnesium chloride solution into high-purity magnesium oxide, and providing the magnesium oxide to the fermentation medium as neutralizing agent, either directly, or after conversion into magnesium hydroxide. These embodiments will be discussed in more detail below.

In one embodiment, the invention pertains to a process for the manufacture of a carboxylic acid comprising the steps of converting magnesium chloride into magnesium oxide by a process comprising the steps of subjecting a magnesium chloride solution to a spray drying step in a spray-drying apparatus, at a temperature in the range of 300-475° C., preferably 350-450° C., resulting in the formation of a spray-dried product comprising 10-80 wt. %, in particular 30-80 wt. %, magnesium oxide and 20-90 wt. %, in particular 20-70 wt. %, of the total of magnesium hydroxychloride and magnesium chloride, and subjecting the product of the spray drying step to a roasting step in a roaster at a temperature of 600-900° C. in the presence of water, resulting in the formation of a magnesium oxide product comprising at least 98 wt. % of MgO, and less than 2% of the total of magnesium hydroxychloride and magnesium chloride (percentages calculated as specified above);

providing the magnesium oxide product comprising at least 98 wt. % of MgO, and less than 2% of the total of magnesium hydroxychloride and magnesium chloride (percentages calculated as specified above) as neutralizing agent to a fermentation step, as such or after a conversion step into magnesium hydroxide by reacting the magnesium oxide product with water, which fermentation step comprises the steps of fermenting a carbon source by means of a micro-organism in a fermentation medium to form carboxylic acid, with the carboxylic acid being converted at least in part by the neutralizing agent, resulting in the formation of a magnesium carboxylate salt.

The amount of magnesium base added during the fermentation step generally is in the range of 0.1 to 4 mole magnesium base per mole carboxylic acid, more specifically in the range of 0.2 to 2 mole magnesium base per mole carboxylic acid.

As indicated above, the product magnesium oxide obtained by the process according to the invention can be used as such. It can also be used after conversion into magnesium hydroxide by reaction with water. The step of converting magnesium oxide into magnesium hydroxide through reaction with water can be carried out by methods known in the art.

The process described above thus yields a fermentation medium comprising magnesium carboxylate. The process according to the invention can also comprise the further steps of subjecting the magnesium carboxylate to an acidification step wherein the magnesium carboxylate is contacted with HCl in an aqueous environment to form an aqueous mixture comprising carboxylic acid and magnesium chloride, subjecting the aqueous mixture comprising carboxylic acid and magnesium chloride to a separation step, to form an effluent comprising carboxylic acid and an aqueous magnesium chloride solution.

The magnesium chloride solution obtained from the separation step can be provided to the process according to the invention. Generally, however, the aqueous magnesium chloride solution derived from the separation step will have a relatively low concentration. Therefore, it may be preferred to subject the aqueous magnesium chloride solution derived from the separation step to one or more concentration steps where water is evaporated, resulting in a more concentrated solution, which is provided to the spray-drying step. In one embodiment an aqueous magnesium chloride solution with a magnesium chloride concentration of 10-30 wt. % is subjected to a concentration step where water is evaporated, resulting in a concentrated magnesium chloride solution with a magnesium chloride concentration of 15-48 wt. %, in particular 35 to 47 wt. %, which is then provided to the spray-drying step. The concentration step or steps can be carried out by methods known in the art, which require no further elucidation here.

As discussed above, HCl-containing gas streams are recovered from the spray-drying step and from the roasting step. In one embodiment, at least part of the HCl derived from one or both of these units is provided to the acidification step, wherein magnesium carboxylate is contacted with HCl in an aqueous environment to form an aqueous mixture comprising carboxylic acid and magnesium chloride. The HCl can be provided to the acidification step in gaseous form. It is also possible, however, to absorb HCl from the HCl containing gas stream into water to form an aqueous HCl solution, and to provide the aqueous HCl solution to the acidification step.

The various steps in the integrated process which are additional to the processing of the magnesium chloride solution will be discussed below.

In the first step a carbon source is subjected to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate.

Fermentation processes for the manufacture of carboxylic acids are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising magnesium carboxylate, biomass, and optionally further components such as impurities like are sugars, proteins, and salts.

If so desired, the fermentation broth may be subjected to a biomass removal step, e.g., a filtration step, before further processing. This is generally preferred for improving product quality. Depending on the carboxylic acid produced, another intermediate step may be separation of solid reaction product, e.g., magnesium carboxylate, from the fermentation broth, before, after, or simultaneous with biomass removal, and optionally subjecting the magnesium carboxylate to a washing step.

Depending on the carboxylic acid produced, another intermediate step may be subjecting the fermentation broth to a concentration step to increase the concentration of magnesium carboxylate in the composition before acidification. This step may be carried out before, after, or simultaneous with biomass removal.

Other intermediate steps, e.g., purification steps, may be carried out as desired, as will be evident to the skilled person.

The next step in the integrated process according to the invention is subjecting the magnesium carboxylate to an acidification step, also sometimes indicated as acidification step, wherein the magnesium carboxylate is contacted with HCl in an aqueous environment to form an aqueous mixture comprising carboxylic acid and magnesium chloride.

There are various ways in which this step can be effected.

The acidification step is typically conducted by bringing the carboxylate salt in contact with an acidic HCl solution. However, in some embodiments it may also be possible to contact the carboxylate salt with gaseous HCl.

The carboxylate salt may be in solid and/or dissolved form. In one embodiment, the carboxylate salt is provided in solid form. In this case, the acidification step is conducted by bringing the carboxylate salt in contact with an acidic solution. The advantage of preparing the aqueous mixture from carboxylate salt in solid form is that very high carboxylic acid concentration can thus be obtained, such as concentration of at least 15 wt. %, in particular at least 25%, up to, e.g. 50 wt. %, or e.g. 40 wt. %.

The carboxylate salt may also be in dissolved form, typically as part of an aqueous solution. In this case, the acidification step can be conducted by bringing the carboxylate salt in contact with an acidic solution or an acidic gas.

The acidification step may also be conducted on a mixture of carboxylic acid and carboxylate salt. Such a mixture may for example be obtained in a low pH fermentation. The mixture may for example be an aqueous suspension.

When acidification of the carboxylate salt is conducted by contacting it with an acidic HCl solution, it preferably has an acid concentration as high as possible. Such a high acid concentration will result in an aqueous mixture with a high carboxylic acid concentration, which is desirable. The acidic solution therefore comprises at least 5 wt. %, more preferably at least 10 wt. % and even more preferably at least 20 wt. % acid, based on the total weight of the acidic solution.

Acidification is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case gaseous HCl is used, it may be contacted by bringing it in contact with a carboxylate solution or suspension. In particular, HCl gas may be blown through the solution or suspension.

Preferably, acidification is conducted at a temperature of 75° C. or less. At higher temperatures, it becomes uneconomical to adapt equipment to the harsh conditions of an acidic environment at high temperatures.

The acidification step results in the formation of an aqueous liquid comprising carboxylic acid and magnesium chloride. This aqueous liquid is subjected to a separation step, optionally after intermediate processing steps have been carried out such as a concentration step. Suitable separation steps are known in the art. The nature of the step to be used depends on the nature and properties of the acids.

Where the carboxylic acid is present in whole or in part as solid in the aqueous liquid, separation can take place using conventional solid-liquid separation methods such as filtration, centrifugation, etc.

Where the carboxylic acid is present in whole or in part as a separate organic phase in the aqueous liquid, separation can take place using conventional liquid-liquid separation methods, e.g., decantation, settling, centrifugation, use of plate separators, use of coalescers, and use of hydrocyclones. An extractant may be added to improve the separation efficiency. Combination of different methods and apparatus may also be used.

Where the carboxylic acid is present dissolved in the aqueous liquid, separation can take place using, e.g., extraction with a suitable extractant.

Where an extractant is present in the process according to the invention, the extractant, which may also be indicated as extraction agent is substantially not miscible with water. The use of an extractant results in the formation of a two-phase system during the separation step which comprises a liquid organic layer comprising extraction agent and carboxylic acid and an aqueous layer comprising dissolved magnesium chloride.

Examples of suitable extractants are aliphatic and aromatic hydrocarbons, such as alkanes and aromatic compounds, ketones, and ethers. Mixtures of various compounds may also be used.

Examples of suitable aliphatic alkanes are C5-C10 straight chain, branched, or cyclic alkanes, e.g., octane, hexane, cyclohexane, 2-ethyl-hexane, and heptane.

Examples of suitable aromatic compounds are C6-C10 aromatic compounds, e.g., toluene, xylenes, and ethylbenzene.

Examples of suitable ketones are C5+ ketones, more in particular C5-C8 ketones in the present invention. C5+ stands for ketones with at least 5 carbon atoms. The use of C9+ ketones is less preferred, The use of methyl-isobutyl-ketone (MIBK) has been found to be particularly attractive.

Examples of suitable ethers are C3-C6 ethers, e.g., methyl tert-butyl ether (MTBE) and diethyl ether (DEE).

After extraction, the carboxylic acid can be separated from the extractant as desired. In one embodiment this can be done by removing the extractant by evaporation. In another embodiment the carboxylic acid can be recovered from the extractant by an extraction with water or another aqueous liquid.

After separation of the carboxylic acid from the salt, the carboxylic acid can be processed as desired. Examples of further processing steps are purification steps such as one or more of washing, active carbon treatment, recrystallization, distillation, and filtration. Where the carboxylic acid is lactic acid, it can be converted to lactide and PLA.

The invention thus also pertains to a process for manufacturing a carboxylic acid comprising the steps of subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate, subjecting the magnesium carboxylate to an acidification step, wherein the magnesium carboxylate is contacted with HCl in an aqueous environment to form an aqueous mixture comprising carboxylic acid and magnesium chloride, subjecting the aqueous mixture comprising carboxylic acid and magnesium chloride to a separation step, resulting in a carboxylic acid and a magnesium chloride solution separated therefrom, subjecting the magnesium chloride solution to a spray drying step at a temperature in the range of 300-475° C., resulting in the formation of a spray-dried product comprising 10-80 wt. % magnesium oxide and 20-90 wt. % of the total of magnesium hydroxychloride and magnesium chloride, subjecting the product of the spray drying step to a roasting step in a roaster at a temperature of 600-900° C. in the presence of water, resulting in the formation of a product comprising at least 98 wt. % of MgO, and less than 2 wt. % of the total of magnesium hydroxychloride and magnesium chloride, wherein the percentages of MgO, magnesium hydroxychloride and magnesium chloride, are calculated on the total of MgO, magnesium hydroxychloride and magnesium chloride.

As will be evident to the skilled person, the further steps and embodiments described herein also apply to this process.

The nature of the carboxylic acid manufactured is not critical to the integrated process according to the invention.

In one embodiment the carboxylic acid is a mono-, di- or tri-carboxylic acid comprising at least 2, but no more than 8 carbon atoms (C2-C8 carboxylic acid). In one embodiment, the carboxylic acid is selected from the group consisting of lactic acid, succinic acid, propionic acid, 3-hydroxypropionic acid, 2-, 3-, and 4-hydroxybutyric acid, citric acid, fumaric acid, itaconic acid, adipic acid, acrylic acid, levulinic acid, maleic acid, 2,5-furandicarboxylic acid, mandelic acid, malic acid, and tartartic acid. Preferably, the carboxylic acid is selected from the group consisting of lactic acid, succinic acid, propionic acid, 3-hydroxypropionic acid, 2-, 3-, and 4-hydroxybutyric acid and citric acid.

In one embodiment, the carboxylic acid is selected from the mono-carboxylic acids with 2-6 carbon atoms. In one embodiment, the monocarboxylic acid with 2-6 carbon atoms does not contain hydroxyl-groups. Within this group, examples of suitable acids are propionic acid, acrylic acid, butyric acid, and valeric acid.

In another embodiment, the monocarboxylic acid contains at least one hydroxyl-group. Within this group, in one embodiment it may be preferred to select the acid from the group of lactic acid, glycolic acid, 3-hydroxypropionic acid, 2-, 3-, and 4-hydroxybutyric acid. In another embodiment within this group it may be preferred to select the acid from the group of glycolic acid, 3-hydroxypropionic acid, and 2-, 3-, and 4-hydroxybutyric acid. In a further embodiment it may be preferred for the acid to be lactic acid.

In another embodiment, the carboxylic acid is a polycarboxylic acid, more in particular a di- or tri-carboxylic acid comprising at least 2, but no more than 6 carbon atoms (C2-6 carboxylic acid). In one embodiment, the polycarboxylic acid is selected from the group consisting of succinic acid, citric acid, fumaric acid, itaconic acid, adipic acid, maleic acid, 2,5-furandicarboxylic acid, malic acid, and tartartic acid. Preferably, the polycarboxylic acid is selected from the group consisting of succinic acid, citric acid, fumaric acid, itaconic acid, adipic acid, and 2,5-furandicarboxylic acid. The polycarboxylic acid may in particular be selected from succinic acid, fumaric acid, itaconic acid, and 2,5-furandicarboxylic acid.

Various aspects of the present invention will be illustrated by the figures discussed below, the invention not being limited thereto or thereby.

FIG. 1 illustrates the process according to the invention. In FIG. 1, a magnesium chloride solution is provided through line (1) to spray drying apparatus (2). A hot gas stream is provided through line (3) and a HCl-containing gas stream is withdrawn through line (4). In the spray-dryer, the magnesium chloride solution is converted to a spray-dried product comprising 10-80 wt. %, in particular 30-80 wt. %, of magnesium oxide and 20-90 wt. %, in particular 20-70 wt. %, of the total of magnesium hydroxychloride and magnesium chloride. The spray-dried product is withdrawn from the spray-dryer through line (5), and provided to roaster (6). A hot gas stream is provided to roaster (6) through line (7), and a HCl-containing gas stream is withdrawn through line (8). If so desired, HCl-containing gas withdrawn from the roaster (7) though line (8) can be provided partially or completely to spray drying apparatus (2).

The product from the roaster comprises at least 98 wt. % of magnesium oxide and less than 2 wt. % of the total of magnesium hydroxychloride and magnesium chloride, and is withdrawn through line (9).

Figure 2:
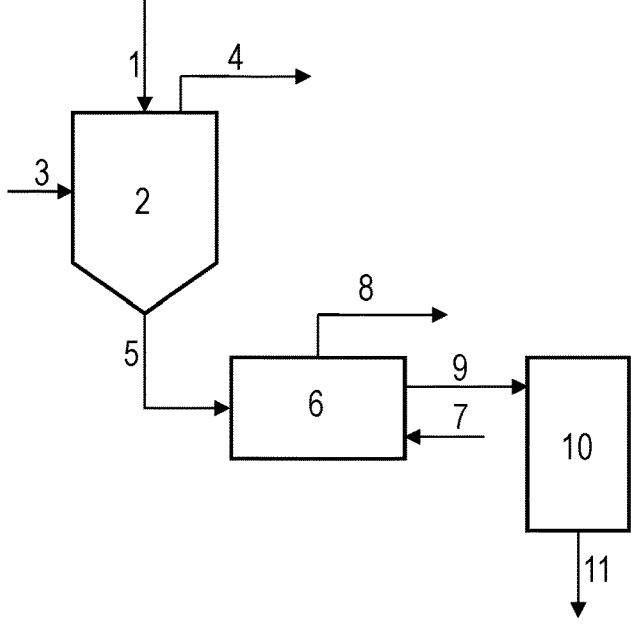
FIG. 2 illustrates the process according to the invention in combination with a fermentation step.

FIG. 2 shows a combination of the process according to the invention as presented in FIG. 1 with a fermentation process. In FIG. 2, the magnesium oxide product that is withdrawn from the roaster through line (9) is provided to fermentation unit (10). This can be done directly, or after conversion of the magnesium oxide product into magnesium hydroxide by reaction with water in a unit not shown.

Fermentation unit (10) is provided with a carbon source and optionally further components such as nutrients through lines not shown. In the fermentation step in fermentation unit (10) a carbon source is fermented by means of a micro-organism in a fermentation broth to form carboxylic acid. At least part of the carboxylic acid is neutralized by a magnesium base, which is the magnesium product derived from the roaster, directly or after having been converted into magnesium hydroxide. The fermentation process in the presence of a magnesium base results in a fermentation medium comprising magnesium carboxylate, which is withdrawn from fermentation unit (10) though line (11).

Figure 3:
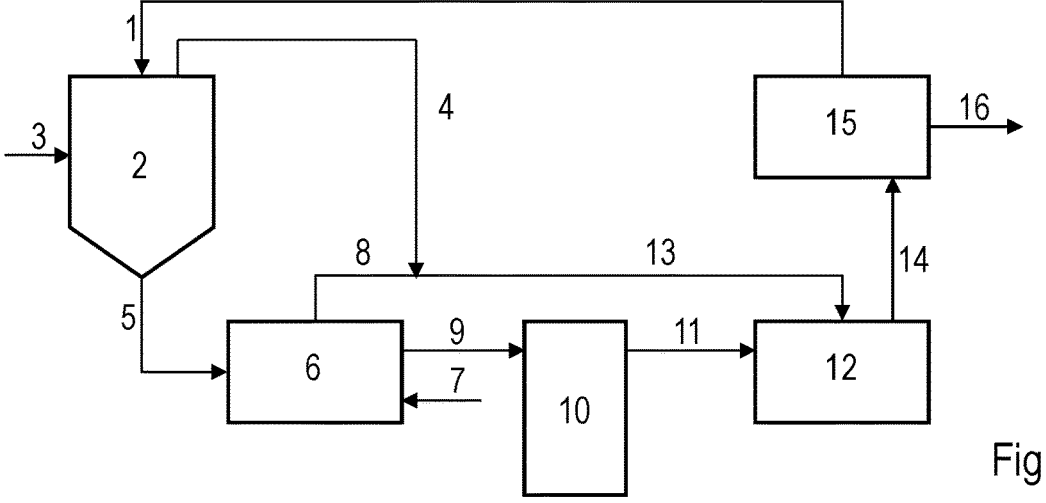
FIG. 3 illustrates the process according to the invention in an integrated process for the manufacture of carboxylic acid.

FIG. 3 illustrates a further integrated process according to the invention, which is based on the process presented in FIG. 2. In the process of FIG. 3, the fermentation medium comprising a magnesium carboxylate salt is provided to an acidification step (12) through line (11). Intermediate steps such as biomass removal or concentration may be carried out, but are not shown. In the acidification step (12) the magnesium carboxylate is contacted with HCl in an aqueous environment to form an aqueous mixture comprising carboxylic acid and magnesium chloride. The HCl is provided through line (13). In the figure the HCl provided through line (13) is a combination of the HCl derived from spray-dryer (1) through line (4) and the HCl derived from roaster (6) through line (8). It will be clear that it is also possible to use only one of these streams, or separately provide the streams to the acidification step (12). The HCl may be provided in the form of a HCl-containing gas stream directly derived from the spray dryer (1) and/or the roaster (6). It may also be provided in the form of an aqueous solution obtained by absorbing the HCl-containing gas stream into an aqueous liquid (e.g., water). This would take place in an absorption step (not shown).

The aqueous mixture comprising carboxylic acid and magnesium chloride is provided to a separation step (15) through line (14). The separation step may be carried out as described above. Separation step (15) results in an effluent comprising carboxylic acid and a magnesium chloride solution. The product carboxylic acid is withdrawn through line (16). The magnesium chloride solution is withdrawn through line (1), and provided to the spray-dryer, as discussed above in the context of FIG. 1.

As will be evident to the skilled person, it is possible to provide only part of the HCl generated in the spray-dryer or roaster to the acidification step, and/or to also provide HCl from other sources. By the same token, it will be evident that it is possible to provide only part of the magnesium oxide product generated in the roaster to the fermentation step.

It will be clear to the skilled person that in the process according to the invention preferred embodiments of various steps can be combined unless they are mutually exclusive.

The present invention is further illustrated by the following examples, without being limited thereto or thereby.

Example 1—Process According to the Invention

A 37-43 wt. % magnesium chloride solution was provided to a spray-dryer and spray-dried at a temperature of 350-420° C. and spray-dried. The product from the spray-drying step contained 50 wt. % magnesium oxide and 50 wt. % of the total of magnesium chloride and magnesium hydroxychloride.

The product from the spray-drying step was subjected to a roasting step for 30 minutes at 800° C., resulting in a product containing 99.2 wt. % of magnesium oxide and 0.8 wt. % of the total of magnesium chloride and magnesium hydroxychloride, calculated on total solid product.

Example 2—Comparative Process

A 37-43 wt. % magnesium chloride solution was provided to a spray-dryer and spray-dried at a temperature of 500° C. The product from the spray-drying step contained 97% magnesium oxide and 3 wt. % of the total of magnesium chloride and magnesium hydroxychloride. This product thus did not have the required degree of purity.

To obtain a magnesium oxide product with the required degree of purity of at least 98 wt. %, it was found that was be necessary to carry out a roasting step for 30 minutes at 800° C., resulting in a product containing 99.2 wt. % of magnesium oxide and 0.8 wt. % of the total of magnesium chloride and magnesium hydroxychloride.

Thus, a comparison between Example 1 according to the invention and Comparative Example 2 shows that spray-drying at 500° C. is insufficient to obtain the desired degree of purity, and that the combination of spray-drying and roasting with a specified degree of conversion in the spray-drying step allows the use of lower temperatures, and thus lower energy consumption, in the spray-drying step.

The invention claimed is:

1. A magnesium oxide product comprising at least 98 wt. % of MgO, and less than 2 wt. % of the total of magnesium hydroxychloride and magnesium chloride, all percentages calculated based on total solid product, wherein the magnesium oxide product has a D50 in the range of 0.5 to 20 microns, and a citric acid reactivity in the range of 75-400 s.

2. A process comprising providing the magnesium oxide product of claim 1 as neutralizing agent to a fermentation step, wherein the fermentation step comprises (a) fermenting a carbon source by means of a micro-organism in a fermentation medium to form carboxylic acid, and (b) converting at least a part of the carboxylic acid by contacting it with the neutralizing agent, resulting in the formation of a magnesium carboxylate salt.

3. The process according to claim 2, further comprising:

subjecting the magnesium carboxylate to an acidification step, wherein the magnesium carboxylate is contacted with HCl in an aqueous environment to form an aqueous mixture comprising carboxylic acid and magnesium chloride, and subjecting the aqueous mixture comprising carboxylic acid and magnesium chloride to a separation step, to form an effluent comprising carboxylic acid and an aqueous magnesium chloride solution.

4. The process according to claim 3, wherein after the separation step the carboxylic acid is subjected to a purification step.

5. The process according to claim 3, wherein a biomass removal step is carried out between the fermentation step and the acidification step.

6. A process according to claim 3, wherein the carboxylic acid is lactic acid, which is subsequently converted into lactide or polylactide.

7. The process according to claim 2, wherein the carboxylic acid is a mono-, di- or tri-carboxylic acid comprising at least 2, but no more than 8 carbon atoms.

8. A process for preparing the magnesium oxide product of claim 1, the process comprising:

subjecting a magnesium chloride solution to a spray drying step at a temperature in the range of 300° C. to 475° C., resulting in the formation of a spray-dried product comprising 10 wt. % to 80 wt. % magnesium oxide and 20 wt. % to 90 wt. % of the total of magnesium hydroxychloride and magnesium chloride, and subjecting the spray dried product to a roasting step in a roaster at a temperature of 600° C. to 900° C. in the presence of water, to form the magnesium oxide product.

9. The process according to claim 8, wherein the spray drying step encompasses subjecting a magnesium chloride solution to a spray drying step in a spray-drying apparatus, at a temperature in the range of 350° C. to 450° C., to form a spray-dried product comprising 30 wt. % to 80 wt. % magnesium oxide and 20 wt. % to 70 wt. % of the total of magnesium hydroxychloride and magnesium chloride.

10. The process according to claim 8, wherein the magnesium chloride solution used in the spray-drying step has a magnesium chloride concentration of 5 wt. % to 48 wt. %.

11. The process according to claim 8, wherein spray-drying is carried out at a temperature in the range of 375° C. to 450° C.

12. The process according to claim 8, wherein the product from the spray-dried product comprises 40 wt. % to 80 wt. % magnesium oxide and 20 wt. % to 60 wt. % of the total of magnesium hydroxychloride and magnesium chloride, all calculated based on the total solids content.

13. The process according to claim 8, wherein the temperature in the roaster is in the range of 700° C. to 850° C.

14. The process according to claim 8, wherein the magnesium oxide product comprises at least 98.5 wt. % of MgO, and less than 1.5 wt. % of the total of magnesium hydroxychloride and magnesium chloride, calculated based on the total solid product.

15. A process comprising:

subjecting a carbon source to a fermentation step to form a carboxylic acid, wherein the fermentation step comprises (a) fermenting a carbon source by means of a micro-organism in a fermentation broth to form carboxylic acid, and (b) neutralizing at least part of the carboxylic acid by adding a magnesium base selected from magnesium oxide and magnesium hydroxide, thereby obtaining a magnesium carboxylate, subjecting the magnesium carboxylate to an acidification step comprising contacting the magnesium carboxylate with HCl in an aqueous environment to form an aqueous mixture comprising carboxylic acid and magnesium chloride, subjecting the aqueous mixture comprising carboxylic acid and magnesium chloride to a separation step, providing a carboxylic acid and a magnesium chloride solution separated therefrom, subjecting a magnesium chloride solution to a spray drying step at a temperature in the range of 300° C. to 475° C., resulting in the formation of a spray-dried product comprising 10 wt. % to 80 wt. % magnesium oxide and 20 wt. % to 90 wt. % of the total of magnesium hydroxychloride and magnesium chloride, and subjecting the spray dried product to a roasting step in a roaster at a temperature of 600° C. to 900° C. in the presence of water, to form the magnesium oxide product of claim 8.

16. The process according to claim 15, wherein after the separation step the carboxylic acid is subjected to a purification step.

17. The process according to claim 15, wherein a biomass removal step is carried out between the fermentation step and the acidification step.

18. The process according to claim 15, wherein HCl is produced during the spray drying step and the roasting step, and at least a part of the is recycled for use in the acidification step.

19. The process according to claim 15, wherein the carboxylic acid is a mono-, di- or tri-carboxylic acid comprising at least 2, but no more than 8 carbon atoms.

20. The process according to claim 15, wherein the carboxylic acid is lactic acid, which is subsequently converted into lactide or polylactide.

* * * * *